(12) United States Patent
Groff

(10) Patent No.: US 9,398,945 B2
(45) Date of Patent: Jul. 26, 2016

(54) VASCULAR IMPLANT RETRIEVAL ASSEMBLY AND METHOD

(71) Applicant: Cook Medical Technologies LLC, Bloomington, IN (US)

(72) Inventor: Hillary Groff, Indianapolis, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 258 days.

(21) Appl. No.: 14/031,158

(22) Filed: Sep. 19, 2013

(65) Prior Publication Data

US 2015/0080938 A1    Mar. 19, 2015

(51) Int. Cl.
*A61F 2/01* (2006.01)
*A61B 17/22* (2006.01)

(52) U.S. Cl.
CPC .......... *A61F 2/01* (2013.01); *A61B 2017/22035* (2013.01); *A61F 2002/011* (2013.01); *A61F 2002/016* (2013.01)

(58) Field of Classification Search
CPC ............... A61F 2002/011; A61F 2/95; A61F 2002/9528; A61F 2002/9511; A61B 17/3468; A61B 2017/22035; A61B 17/221; A61B 17/22031; A61B 17/32056
See application file for complete search history.

(56) References Cited

U.S. PATENT DOCUMENTS

| | | | |
|---|---|---|---|
| 5,423,830 A | 6/1995 | Schneebaum et al. |
| 5,562,678 A | 10/1996 | Booker |
| 5,741,271 A | 4/1998 | Nakao et al. |
| 5,800,457 A | 9/1998 | Gelbfish |
| 5,893,869 A | 4/1999 | Barnhart et al. |
| 6,068,603 A | 5/2000 | Suzuki |
| 6,517,550 B1 | 2/2003 | Kónya et al. |
| 6,966,914 B2 | 11/2005 | Abe |
| 7,201,768 B2 | 4/2007 | Diaz et al. |
| 7,534,252 B2 | 5/2009 | Sepetka et al. |
| 7,691,110 B2 | 4/2010 | Secrest et al. |
| 7,955,345 B2 | 6/2011 | Kucharczyk et al. |
| 8,092,470 B2 | 1/2012 | Miyamoto et al. |
| 2009/0076585 A1 | 3/2009 | Hendriksen et al. |
| 2012/0184987 A1 | 7/2012 | Sirota |

*Primary Examiner* — Katherine M Shi
*Assistant Examiner* — Michael Mendoza
(74) *Attorney, Agent, or Firm* — Brinks Gilson & Lione

(57) ABSTRACT

A retrieval assembly for retrieving an implanted device includes an outer catheter; an interior tube arrangement with a first tube extending through the catheter lumen and having a first distal end, and with a second tube having extending through the catheter lumen outside the first tube. The second tube has a distal portion extending distally past the first distal end with a bend toward the first tube axis and with a second distal end. An entangling element is configured to be advanced through the second tube past the second distal end and to be at least partially retracted into the second tube. A withdrawal tool configured for engaging the implanted device and for at least partially retracting the implanted device into the first tube. The entangling element may have a distal flexible coil, and the withdrawing tool may have a distal pickup hook.

14 Claims, 5 Drawing Sheets

VASCULAR IMPLANT RETRIEVAL ASSEMBLY AND METHOD

TECHNICAL FIELD

The present disclosure relates generally to retrieval mechanisms and methods for retrieving vascular implanted devices. More particularly, the present disclosure relates to retrieving a vena cava filter from a body vessel.

BACKGROUND

A variety of vascular implants are well known and widely used. Vascular filters are commonly used for filtration of blood in the inferior vena cava of human patients. Stents may be used at various locations throughout a patient's vasculature to maintain or enhance blood flow where blockage has occurred. Many vascular implants are not intended for permanent placement, and may be removed after the patient's need for them has ended or upon conclusion of the service life of the vascular implant. In the case of vascular filters patients may be equipped with a vascular filter for surgical recovery or during other relatively long periods of relative immobility associated with blood clot formation. Certain stents may become less effective over time. In either case, usual protocol is removal of the vascular implant from the patient if practicable.

Different techniques and mechanisms for the removal of vascular implants from a patient have been proposed over the years. It has been observed that endothealization of portions of certain vascular implants may occur in vivo. In general terms, endothealization is the growth of excess vascular tissue about portions of the vascular implant contacting the associated vascular wall. As a result of endothealization, portions of a vascular implant can become lodged in or against a vascular wall. This phenomenon can make it difficult to snare a hook on a vascular implant with a conventional removal device and the vascular implant may further not have a proper orientation of the vascular implant for collapsing with a sheath.

SUMMARY OF THE DISCLOSURE

According to a first aspect, a retrieval assembly for retrieving an implanted device comprises an outer catheter; an interior tube arrangement with a first tube extending through the catheter lumen and having a first distal end, and with a second tube having extending through the catheter lumen outside the first tube. The second tube has a distal portion extending distally past the first distal end with a bend toward the first tube axis and with a second distal end. An entangling element is configured to be advanced through the second tube past the second distal end and to be at least partially retracted into the second tube. A withdrawal tool configured for engaging the implanted device and for at least partially retracting the implanted device into the first tube.

The entangling element preferably has a stiffness suitable for entangling an implanted device and for moving the implanted device toward the first distal end.

For easier movement of the entangling device, the bend may be shaped as sweep elbow. Alternatively or additionally, the bend may have a bend angle of more than 30° and less than 90°.

For easier manipulation with one joint operating handle, the first and second tubes may be connected to each other proximally from the first distal end and axially movable relative to the outer catheter. The entangling element may comprise a distal coil. The distal coil is preferably flexible and resilient and deflects under its own weight over a length of no more than 3 cm.

The withdrawal tool comprises a distal pickup hook with at least one hook finger. The pickup hook may have two hook fingers pointing in radially opposite directions for an improved chance of engaging the implanted device. An axial offset between the hook fingers reduces the radial dimension of the pickup hook.

According to another aspect, a method of retrieving an implanted device from a body vessel comprises the steps of distally advancing an outer catheter into a body vessel near the implanted device to a position, in which a distal end of the outer catheter is proximal from the implanted device; distally advancing an interior tube arrangement through the outer catheter beyond the distal end of the outer catheter, the interior tube arrangement having a first tube and a second tube, the first tube having a first tube axis extending through the catheter lumen and having a first distal end, the second tube having a second tube axis extending through the catheter lumen outside the first tube, the second tube having a distal portion extending distally past the first distal end with a bend toward the first tube axis, the distal portion terminating in a second distal end; distally advancing an entangling element through the second tube past the second distal end; entangling the implanted device with the entangling element; withdrawing the entangling element into the second tube and moving the implanted device with the entangling element until the implanted device is in a position suited for engagement with a tool; distally advancing a withdrawal tool through the first tube past the first end; engaging the implanted device with the withdrawal tool; at least partially retracting the implanted device into the first tube; proximally retracting the interior tube arrangement and the implanted device into the outer catheter; and proximally retracting the outer catheter from the body vessel. The entangling tool may thus be used to align a filter or another misaligned implanted device with the body vessel to move the implanted device into a position and orientation that allows for engaging a retrieval attachment, such as a retrieval hook.

The implanted device may be partially or completely retracted into the first tube before the interior tube arrangement is retracted into the outer catheter.

Further details and advantages become apparent from the following description of the drawings disclosing various illustrative embodiments of the retrieval device and method. The drawings are provided for illustrative purposes only and are not intended to limit the scope of the claims.

DETAILED DESCRIPTION

Figure 1:
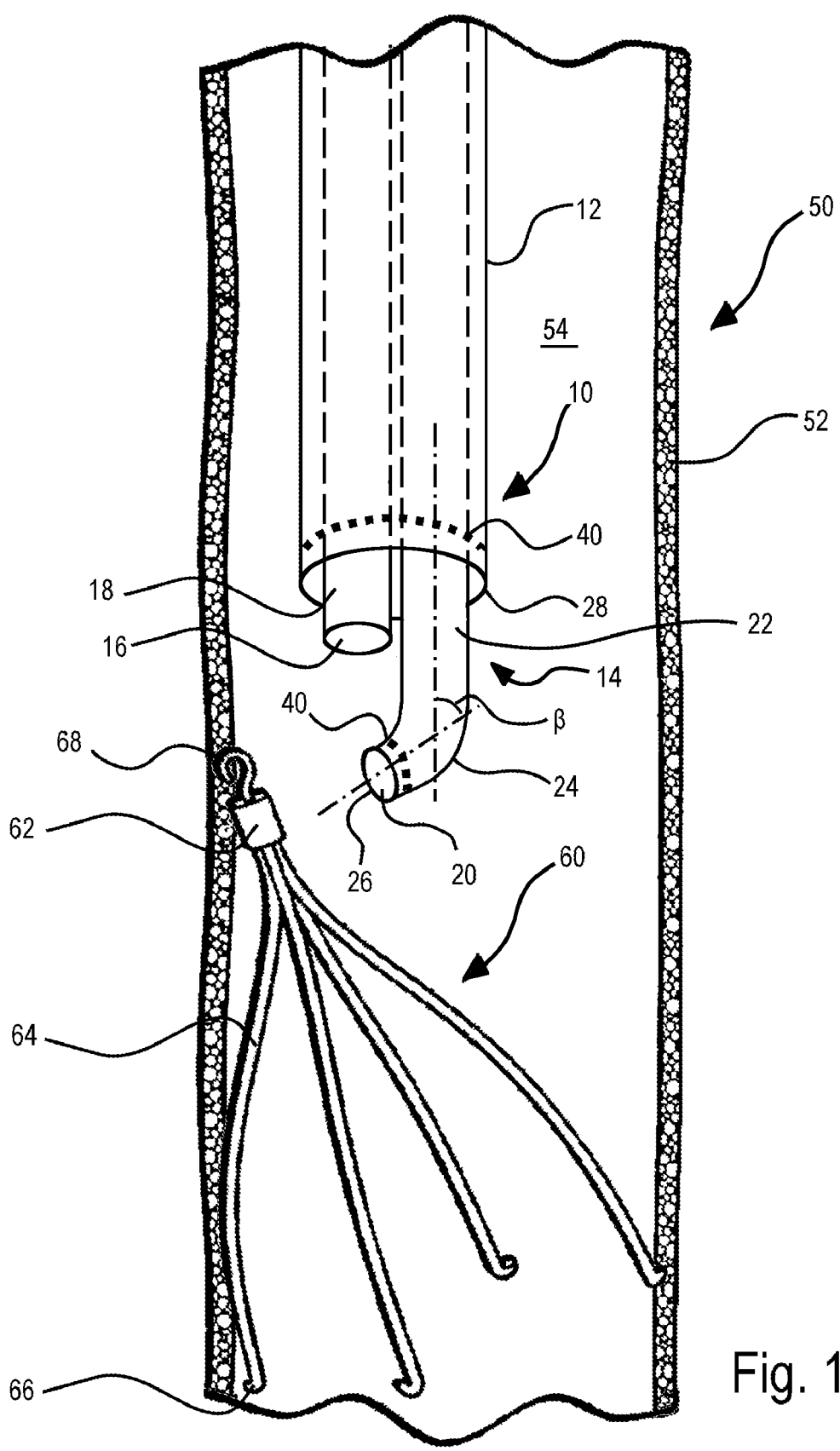
FIG. 1 shows one stage of a vascular implant retrieval procedure with a vascular implant retrieval device according to one aspect of the disclosure.

FIG. 1 schematically shows a longitudinal cut through a body vessel 50 having a generally tubular vessel wall 52 enclosing a vessel lumen 54. Disposed in the vessel lumen 54 is a vascular implant, shown as a filter 60. The filter 60 has a generally conical or bell shape with a filter hub 62 and filter struts 64 extending distally from one axial side of the filter hub 62 and having distally increasing radial distances to each other along their length. The filter struts 64 have distal anchor hooks 66 for anchoring the struts 64 in the vessel wall 52. A retrieval hook 68 is secured to the axially proximal side of the filter hub 62.

FIG. 1 shows a situation, in which the filter 60 is in misalignment with the body vessel 50. Instead of being axially aligned with the body vessel 50, the filter 60 is tilted so that the retrieval hook 68 is partially embedded in body tissue. In the example shown, the open side of the retrieval hook 68 is inaccessible for a retrieval snare so that a conventional retrieval of the filter 60 is at least very difficult or even impossible.

According to one aspect of the present disclosure, a retrieval assembly 10 for vascular implants is provided. The retrieval assembly comprises an outer sheath or catheter 12 and an interior tube arrangement 14 having a first lumen 16 and a second lumen 18 extending beside each other through the catheter 12. The first lumen 16 is formed by a first bendable tube 18 that has a relaxed state with constant diameter and rotational symmetry. The second lumen 20 is formed by a second bendable tube 22 distally extending beyond the first tube 18 with a distal portion 24. The second tube 22 has a relaxed state, in which the distal portion 24 forms a rounded bend toward the first tube 18.

The bend of the distal portion 24 is preferably formed as a sweep elbow, meaning that the inner bend radius is larger than zero. Further, the total bend angle β defined by the longitudinal central axes through the second tube proximal from the distal portion 24 and through the distal end 28 is preferably less than 90° to ease a movement of a tool through the bend by pushing the tool from the proximal end of the first tube, as will be explained farther below. The bend angle β may, for example be within a range of 30° and 80°. In the embodiment shown, the bend angle β is about 50° within ±10°. The distal end 26 of the second tube 22 thus radially overlaps with a distal projection of the first lumen 16.

In the step illustrated in FIG. 1, the outer catheter 12 of the retrieval assembly 10 is introduced into the body vessel from the proximal side, i.e. the side at which the retrieval hook 68 of the vascular implant, here filter 60, is located. The distal end 28 of outer catheter 12 is placed near, but proximal from the retrieval hook 68 of filter 60. Subsequently, the interior tube arrangement 14 including first tube 18 and second tube 22 is distally advanced through the distal end 28 of the outer catheter 12 until a portion of the filter 60 is within the trajectory of the distal portion 24 of the second tube 22, i.e. in a direction, in which the distal end 26 points.

For monitoring a proper placement of the outer catheter 12 and the interior tube arrangement 14, appropriate markers 40 may be applied to at least the distal end 28 of the outer catheter and the distal end 26 of the second tube. The markers 40 may be chosen to be detectable with a conventional imaging technique, for example by x-ray via radiopacity or by ultrasound via echogenicity.

Figures 5, 6:
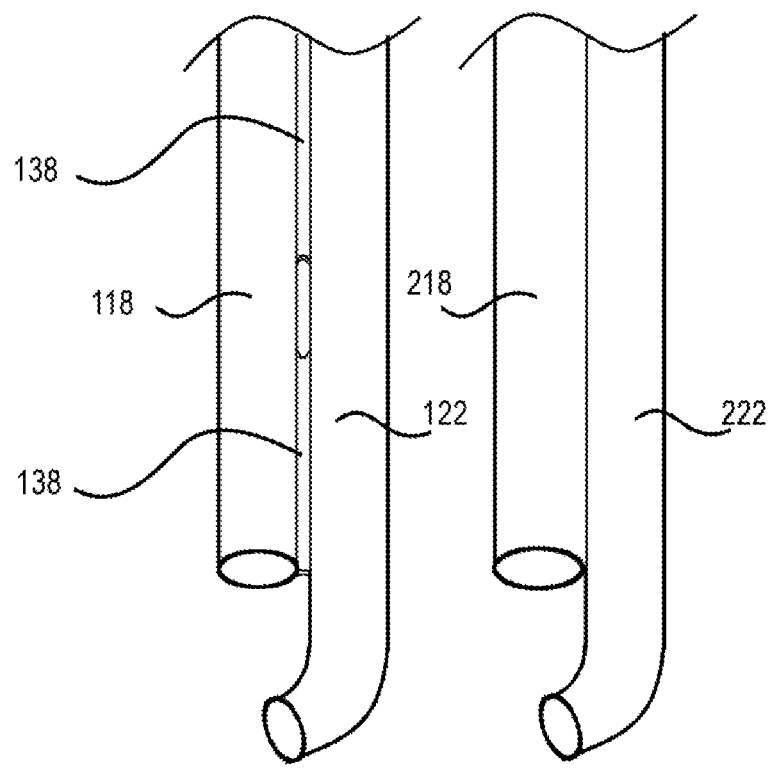
FIG. 5 shows a partial view of a vascular implant retrieval device according to a second embodiment of the disclosure.
FIG. 6 shows a further partial view of the vascular implant retrieval device according to a third embodiment of the disclosure.

Because for the described method, the first tube 18 and the second tube 22 may be jointly moved in the same direction and at the same speed, the first tube 18 may be connected to the second tube 22. FIG. 5, for example, shows an alternative embodiment of the interior tube arrangement 14, in which the first tube 118 is connected with the second tube 122 via at least one web 138 extending between the first tube 118 and the second tube 122 along at least a portion of their parallel length, i.e. the length along which the tubes 118 and 122 extend parallel to each other. While FIG. 5 shows a plurality of webs 138, one continuous web 138 may extend between the first tube 118 and the second tube 122 along a part or all of the parallel length.

In a further alternative embodiment of the interior tube arrangement 14 according to FIG. 6. The first tube 218 and the second tube 222 may be in tangential contact with each other and attached to each other over their entire parallel length. By bringing the tubes 218 and 222 close together, a larger diameter is available for the first tube 218, for example, compared to the previously shown embodiments. Coupling the first tube 118 or 218 with the second tube 122 or 222 has the benefit that the interior tube arrangement 114 or 214, respectively, can be jointly manipulated with one proximal operating arrangement, such as a handle (not shown).

Either one of the embodiments of FIGS. 5 and 6 may replace the embodiment of FIGS. 1 through 4 for performing the method shown in FIGS. 1 through 4.

Figure 2:
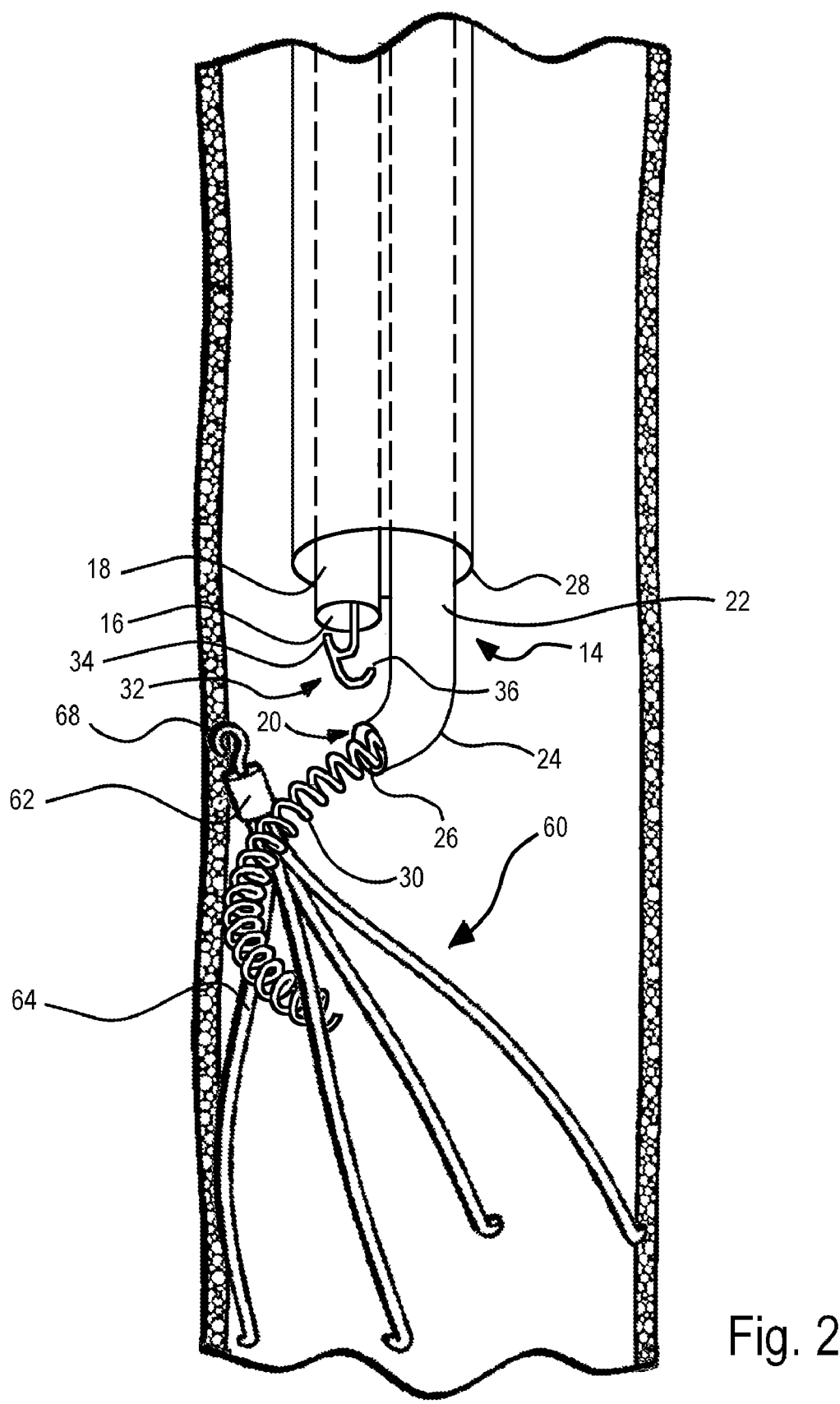
FIG. 2 shows a further stage of the vascular implant retrieval procedure of FIG. 1.

Now referring to FIG. 2, an elongated entangling element is distally advanced through the lumen 20 of the second tube 22. In FIG. 2, the elongated entangling element is shown as a coil 30. The coil 30 is made of a flexible, resilient material, such as a thin wire. The dimensions of the coil wire and the coil diameter are chosen to make the coil 30 relatively soft in the sense that it will deflect under its own weight of a free length of no more than 2-3 cm. The total length of the coil 30 in a relaxed, i.e. unstretched, state is preferably 5-10 cm, which is long enough to perform the function of entangling the filter 60 as described below, but short enough not to catch on the vessel wall 52. Thus, while the coil 30 is stiff enough to be projected from the distal portion 24 of the second tube 22 and to resist plastic straightening of its windings when pulled, it is soft enough to wind around the hub 62 or upper portions of the struts 64 of filter 60.

In FIG. 2, for example, the coil 30 extends from the second tube 22 past the filter hub 62 and between the struts 64. The exact path of the coil 30 may vary from the one shown. It is preferable, however, that the coil 30 engages a portion of the filter 60 that is near the retrieval hook 68 to exert a pull force in the proper direction, as will be explained below.

A pickup tool shown as a pickup hook 32 is subsequently or simultaneously distally advanced through the lumen 16 first tube 18. The pickup hook 32 as shown comprises two hook fingers 34 and 36 that are open in opposite radial directions for receiving the retrieval hook 68. The dual hook fingers 34 and 36 increase the odds of successfully catching the retrieval hook 68 hook because the hook fingers 34 and 36 allow for different angular orientations of the retrieval hook 68. In the example shown in FIG. 2, the hook fingers 34 and 36 are longitudinally offset from each other to reduce the radial overall dimension of the pickup hook 32.

Figure 7:
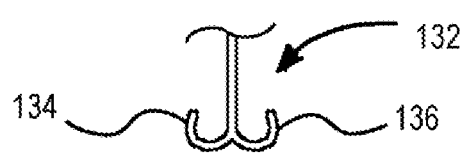
FIG. 7 shows another partial view of the vascular implant retrieval device according to a fourth embodiment of the disclosure.

An alternative embodiment of a suitable pickup hook 132 is, for example, shown in FIG. 7. In FIG. 7, the hook fingers 134 and 136 are arranged in the same axial position, radially opposite from each other. The structure shown in FIG. 7 is suitable for situations, in which the hook fingers 134 and 136 are small enough to fit side-by-side in the first lumen 16 of the first tube 18 without becoming jammed.

Figure 3:
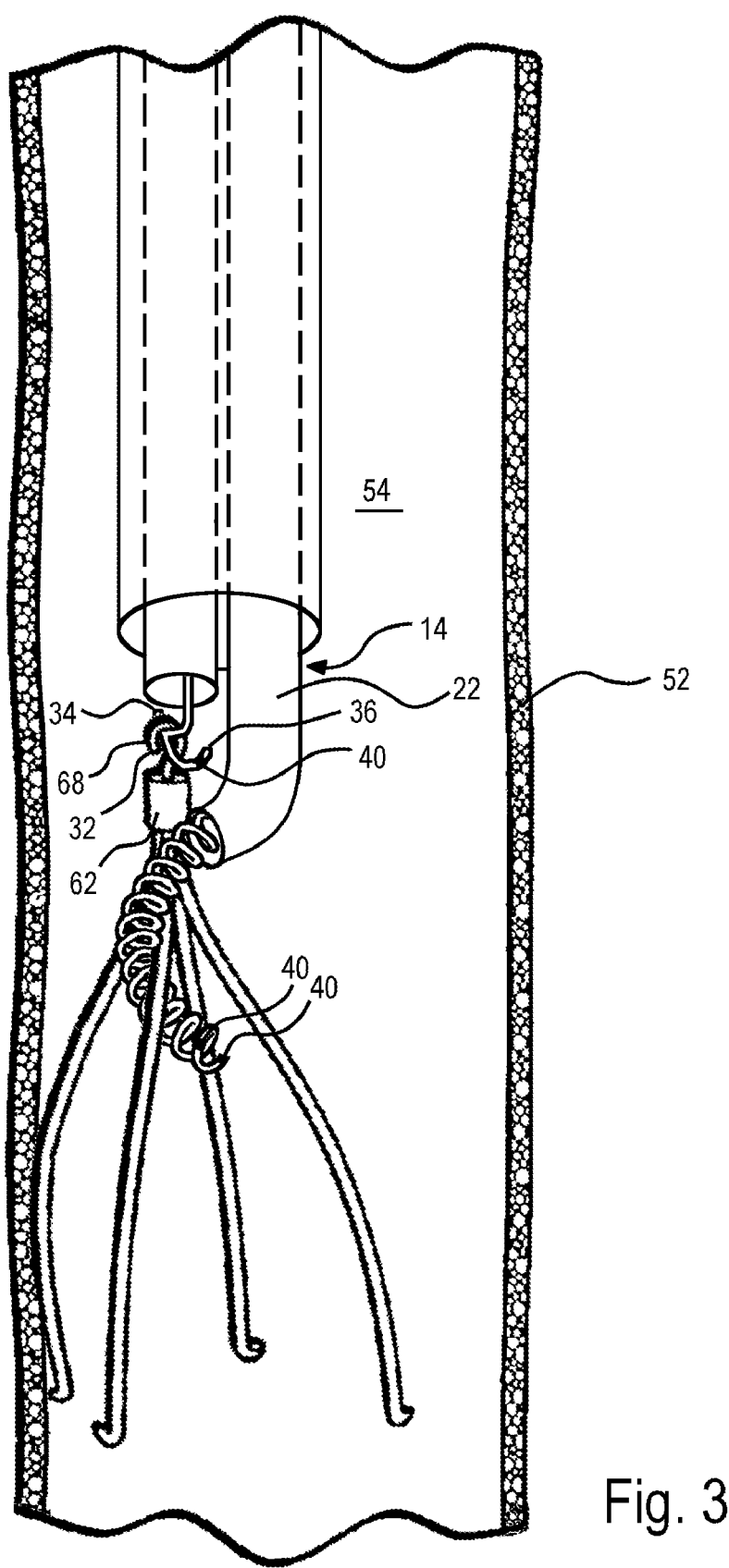
FIG. 3 shows a yet further stage of the vascular implant retrieval procedure of FIG. 1.

Now referring to FIG. 3, the entangling element shown as coil 30, after engaging the filter 60 by entangling, is proximally withdrawn through the second tube 22. The coil 30 is resilient to a degree that it can withstand the pull force required to dislodge the retrieval hook 68 from the body tissue or from the vessel wall 52 without suffering a plastic deformation that completely straightens the coil 30. A minor plastic deformation is harmless as long as the coil 30 is further capable of maneuvering the filter 60 without slipping out of the engagement with the filter 60. The coil 30, being latched onto the filter 60 near the retrieval hook 68 or at least near the hub 62, further exerts a torque onto the filter 60 that rotates the filter 60 about a horizontal axis to bring the filter 60 into alignment with the vessel lumen 54.

The coil 30 and the pickup hook 32 are then manipulated relative to each other until the retrieval hook 68 engages one of the hook fingers 34 and 36 of the pickup hook 32. This manipulation may entail longitudinal movements of the coil 30 or of the pickup hook 32, or both, for improving the placement of the retrieval hook 68 relative to the pickup hook 32. Further, the pickup hook 32 may be rotated if desired to point the hook fingers 34 and 36 radially perpendicular to the retrieval hook. Because this manipulation involves precise movements, the pickup hook 32 or the coil 30, or both, may bear markers 40 of the same type as previously mentioned in connection with the outer catheter 12 and the interior tube arrangement 14 for improved monitoring. In FIG. 3, the markers 40 are indicated with an arbitrary pattern. The shape and position of the markers 40 may be adapted for certain functionalities and may, for example, have a shape and position that additionally allow the detection of a rotational position as generally known in the art.

Figure 4:
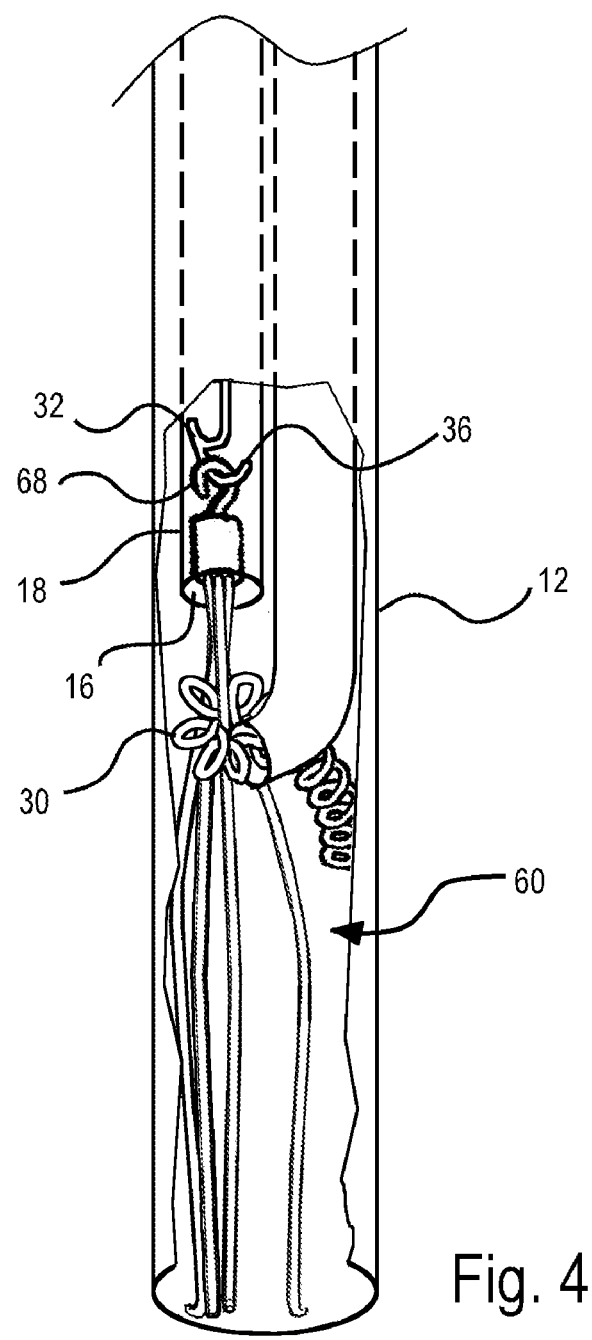
FIG. 4 shows yet a further stage of the vascular implant retrieval procedure of FIG. 1.

Now referring to FIG. 4, once the retrieval hook 68 and the pickup hook 32 are engaged with each other, the pickup hook 32 is proximally withdrawn into the first tube 18. The pickup hook 32 is withdrawn at least far enough to place both the pickup hook 32 and the retrieval hook 68 inside the lumen 16 of the first tube 18, for example, as shown in FIG. 4. During this withdrawal operation, the coil 30 does not require an external manipulation. Due to the flexibility and softness of the coil 30, it may follow the movement of the filter 60, but such a movement is not essential because the filter 60 is now engaged with the pickup hook 32.

In FIG. 4, the retrieval hook 68 engages the lower hook finger 36, while in FIG. 3, the retrieval hook 68 is shown engaging the upper hook finger 34. As mentioned above, the opposite orientations of the two hook finger 34 and 36 are provided to ease engagement of the retrieval hook 68, and both situations shown in FIG. 3 and in FIG. 4, respectively, are equally suited for performing the disclosed method of retrieving the filter 60.

After pulling the retrieval hook 68 into the first tube 18, the entire filter 60 may likewise be proximally retracted into the first tube 18 before proximally withdrawing the interior tube arrangement 14 into the outer catheter 12 until the complete interior tube arrangement 14 including the filter 60 is accommodated inside the outer catheter 12 (not shown).

Alternatively, after pulling the retrieval hook 68 into the first tube 18, as shown in FIG. 5, the interior tube arrangement 14 may be proximally withdrawn relative to the outer catheter 12 far enough that the portions of the filter 60 that may protrude distally from the first tube 18 are completely disposed within the outer catheter 12.

While the above-described method only requires relative movements of the individual parts of the retrieval assembly, it may be beneficial to arrange most of these movements in a way that does not require an axial movement of the filter 60 itself to reduce trauma to the vessel wall 52 by the anchor hooks 66. Thus, for example, once the pickup hook 32 and the retrieval hook 68 are engaged, it may be preferable to accommodate the engaged hooks 32 and 68, and possibly the entire filter 60, inside the first tube 18 by distally moving the interior tube arrangement 14 instead of proximally pulling the filter 60. Likewise, the outer catheter 12 may be moved distally to accommodate the interior tube arrangement 14 and the filter 60.

Once the filter 60 and the interior tube arrangement 14 are completely surrounded by the outer catheter 12, the outer catheter 12, along with the filter 60 and the interior tube arrangement 14, may be proximally withdrawn from the body vessel 50.

While the above method was described by the example of the filter 60, it is suited for the retrieval of any implanted device with a retrieval hook or retrieval element, such as a loop, that can be engaged by the pickup hook 32 if the implanted device has a radial dimension or is collapsible to a radial dimension that can be accommodated in the outer catheter 12.

The foregoing description of the drawings is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

The invention claimed is:

1. A retrieval assembly for retrieving an implanted device, the retrieval assembly comprising:
    an outer catheter for insertion into a patient, the outer catheter having a distal catheter end and a catheter lumen, the catheter lumen defining a catheter axis;
    an interior tube arrangement with a first tube and a second tube, the first tube having a first tube axis extending through the catheter lumen and having a first distal end, the second tube having a second tube axis extending through the catheter lumen outside the first tube, the second tube having a distal portion extending distally past the first distal end with a bend toward the first tube axis, the distal portion terminating in a second distal end;
    an entangling element configured to be advanced through the second tube past the second distal end and to be at least partially retracted into the second tube, the entangling element having a stiffness suitable for entangling an implanted device and for moving the implanted device toward the first distal end;
    and a withdrawal tool configured to be distally advanced through the first tube past the first end and to be proximally retracted into the first tube, the withdrawal tool configured for engaging the implanted device and for at least partially retracting the implanted device into the first tube.

2. The assembly according to claim 1, wherein the entangling element has a stiffness suitable for entangling an implanted device and for moving the implanted device toward the first distal end.

3. The assembly according to claim 1, wherein the bend is a sweep elbow.

4. The assembly according to claim 1, wherein the bend has a bend angle of more than 30° and less than 90°.

5. The assembly according to claim 1, wherein the first and second tubes are connected to each other proximally from the first distal end and axially movable relative to the outer catheter.

6. The assembly according to claim 1, wherein the entangling element comprises a distal coil.

7. The assembly according to claim 6, wherein the distal coil is flexible and resilient and deflects under its own weight over a length of no more than 3 cm.

8. The assembly according to claim 1, wherein the withdrawal tool comprises a distal pickup hook with at least one hook finger.

9. The assembly according to claim 8, wherein the pickup hook has two hook fingers pointing in radially opposite directions.

10. The assembly according to claim 9, wherein the hook fingers are axially offset from each other.

11. A method of retrieving an implanted device from a body vessel, the method comprising:
   distally advancing an outer catheter into a body vessel near the implanted device to a position, in which a distal end of the outer catheter is proximal from the implanted device;
   distally advancing an interior tube arrangement through the outer catheter beyond the distal end of the outer catheter, the interior tube arrangement having a first tube and a second tube, the first tube having a first tube axis extending through the catheter lumen and having a first distal end, the second tube having a second tube axis extending through the catheter lumen outside the first tube, the second tube having a distal portion extending distally past the first distal end with a bend toward the first tube axis, the distal portion terminating in a second distal end;
   distally advancing an entangling element through the second tube past the second distal end;
   entangling the implanted device with the entangling element;
   withdrawing the entangling element into the second tube and moving the implanted device with the entangling element until the implanted device is in a position suited for engagement with a tool;
   distally advancing a withdrawal tool through the first tube past the first end;
   engaging the implanted device with the withdrawal tool;
   at least partially retracting the implanted device into the first tube;
   proximally retracting the interior tube arrangement and the implanted device into the outer catheter; and
   proximally retracting the outer catheter from the body vessel.

12. The method of claim 11, wherein in the step of at least partially retracting the implanted device into the first tube, the implanted device is completely retracted into the first tube.

13. The method of claim 11, wherein the entangling element includes a distal coil.

14. The method of claim 12, wherein the withdrawal tool includes a distal pickup hook.

* * * * *